United States Patent
Bohling et al.

(10) Patent No.: US 8,703,112 B2
(45) Date of Patent: *Apr. 22, 2014

(54) LOW ODOR COATING COMPOSITIONS AND PAINTS

(75) Inventors: James Bohling, Lansdale, PA (US); Paul Doll, North Wales, PA (US); David Frattarelli, West Chester, PA (US); Alvin Maurice, Lansdale, PA (US)

(73) Assignee: Rohm and Haas Company, Philadelphia, PA (US)

(*) Notice: Subject to any disclaimer, the term of this patent is extended or adjusted under 35 U.S.C. 154(b) by 597 days.

This patent is subject to a terminal disclaimer.

(21) Appl. No.: 12/924,648

(22) Filed: Oct. 1, 2010

(65) Prior Publication Data

US 2012/0083021 A1    Apr. 5, 2012

(51) Int. Cl.
*A61K 31/74* (2006.01)
*A61K 38/43* (2006.01)

(52) U.S. Cl.
USPC ..................... 424/78.09; 424/94.1

(58) Field of Classification Search
None
See application file for complete search history.

(56) References Cited

U.S. PATENT DOCUMENTS

| 5,145,890 | A | * | 9/1992 | Frederick et al. | 524/21 |
| 5,422,269 | A | * | 6/1995 | Nicks et al. | 435/262.5 |
| 5,856,150 | A | | 1/1999 | DiGregorio | |
| 6,040,368 | A | * | 3/2000 | Maver et al. | 524/110 |
| 7,285,590 | B2 | * | 10/2007 | Holub et al. | 524/460 |
| 2005/0171274 | A1 | * | 8/2005 | Even | 524/556 |
| 2008/0182929 | A1 | * | 7/2008 | Strepka et al. | 524/291 |

FOREIGN PATENT DOCUMENTS

WO    9115520 A1    10/1991

* cited by examiner

*Primary Examiner* — Debbie K Ware
(74) *Attorney, Agent, or Firm* — Reid S. Willis

(57) ABSTRACT

This invention provides low odor stable coating compositions, and methods of their production. The stable aqueous coating compositions and paints comprise one or more emulsion-polymerized addition polymer and one or more carboxylesterase enzyme having an ester hydrolysis activity in the composition of less than 0.03 micromole/minute, wherein the aqueous coating composition has a headspace volatile organic compound (VOC) content, as measured by headspace gas chromatography-mass spectrometry (GC-MS) at 33° C., of less than 10 ppm of the one or more organic carboxylester with a normal boiling point of less than 150° C. and more than 50 ppm of the one or more mono-alcohol with a formula molecular weight of less than 76.

7 Claims, No Drawings

LOW ODOR COATING COMPOSITIONS AND PAINTS

This application claims the benefit of priority under 35 U.S.C. §119(e) of U.S. Provisional Patent Application No. 61/277,879 filed on Sep. 30, 2009.

This invention relates to low odor stable coating compositions, including low odor stable paints, and methods of their production. More specifically, it relates to stable aqueous coating compositions and paints comprising one or more emulsion-polymerized addition polymer and one or more carboxylesterase enzyme having an ester hydrolysis activity in the composition of less than 0.03 micromole/minute, wherein the aqueous coating composition has a headspace volatile organic compound (VOC) content, as measured by headspace gas chromatography-mass spectrometry (GC-MS) at 33° C., of less than 10 ppm of the one or more organic carboxylester with a normal boiling point of less than 150° C. and more than 50 ppm of the one or more mono-alcohol with a formula molecular weight of less than 76.

Paint formulators have made strides to reduce or eliminate formulation additives which contribute to odor in waterborne paints, however, the presence of carboxylester compounds has remained problematic. Such compounds may be present in small quantities in the emulsion polymer latex (for example, on the order of 50 to 400 ppm in the headspace) which functions as a binder in the paint. These carboxylester compounds usually derive from unreacted carboxylester monomer remaining from the polymerization reaction that forms the latex polymer and are carried into the final coating composition or paint along with the binder. The inventive low odor coating compositions and low odor paints are obtained by reducing the carboxylester content by contacting the aqueous emulsion polymer with a carboxylesterase, either before, during, or after formulating the coating composition or paint.

BACKGROUND OF THE INVENTION

Emulsion-polymerized addition polymers are prepared by the polymerization of ethylenically-unsaturated monomers using ionic- or free radical-initiated and propagated reactions. In most cases these reactions will not proceed to the point of 100% conversion of the ethylenically-unsaturated monomer to polymer within a reasonable time. Elimination of the residual monomer may be desirable due to odor, instability, or toxicity, for example, resulting from the residual monomer. Subsequent elimination of the remaining ethylenically-unsaturated monomer by conversion to polymer by methods such as, for example, heating for prolonged periods, with or without the addition of an ion- or a free radical-source; or physical removal of residual ethylenically-unsaturated monomer by methods such as, for example, vacuum stripping and steam sparging; or conversion to a less undesirable species such as, for example, conversion to a non-volatile adduct have all been disclosed in the past. However, concerns about the toxicity or odor of organic compounds in general, and of ethylenically-unsaturated monomers in particular, have lowered the level of residual ethylenically-unsaturated monomer which is acceptable in emulsion-polymerized addition polymers, and coatings that contain them, to levels which are frequently difficult and costly to achieve by conventional techniques. One category of ethylenically-unsaturated monomers is carboxylester monomers wherein at least one carboxylester grouping, —COOR, is present. In addition, ethylenically-unsaturated monomers may contain, as an impurity, saturated organic carboxylesters, i.e., compounds bearing at least one ester grouping which compounds are not ethylenically-unsaturated, and which persist in the emulsion polymer latex. Further, polymerization adjuvants may introduce additional organic carboxylesters, i.e., compounds bearing at least one ester grouping but which may not be ethylenically-unsaturated monomers. Such compounds, too, may give rise to concerns about toxicity or odor and should be eliminated from low odor coating compositions and low odor paints.

U.S. Pat. No. 5,422,269, to Nicks et al., discloses a method for reducing the residual levels of monomeric ethylenically-unsaturated carboxylic acid esters, such as alkyl acrylates and alkyl methacrylates, in surfactant stabilized dispersions of polymer of these monomers, such as latices or products formulated from latices. The residual monomer content is reduced by treatment with a hydrolytic enzyme, particularly a lipase or esterase, which treatment reduces the odor arising from the presence of the monomers. However, this disclosure does not discuss properties of formulated coatings or paints and the methods described therein have failed to result in any commercially viable low odor paints because the enzymes described therein and the levels of use disclosed therein result in enzyme degradation of paints. That is, the enzyme is active in attacking esters present in useful paint formulation components.

It is, therefore, an object of this invention to provide stable aqueous coating compositions and paints having low odor. It is an additional object of this invention to provide stable coating compositions and paints having a headspace VOC level, as measured by headspace GC-MS at 33° C., of less than 10 ppm, and preferably less than 5 ppm, of organic carboxylester. It is a further object of this invention to provide stable coating compositions and paints having a headspace VOC level of less than 10 ppm, and preferably less than 5 ppm, of organic carboxylester, and an ester hydrolysis enzyme activity of less than 0.03 micromole/minute. It is also an object of this invention to provide a method for producing stable coating compositions and paints having low odor, and having a headspace VOC level of less than 10 ppm, and preferably less than 5 ppm, of organic carboxylester.

SUMMARY OF THE INVENTION

This invention provides stable low odor aqueous coating compositions comprising: i) one or more emulsion-polymerized addition polymer; ii) one or more carboxylesterase enzyme having an ester hydrolysis activity in the composition of less than 0.03 micromole/minute, preferably less than 0.02 micromole/minute; iii) one or more mono-alcohol with a formula molecular weight of less than 76; and iv) optionally, one or more organic carboxylester with a normal boiling point of less than 150° C.; wherein the aqueous coating composition has a headspace volatile organic compound (VOC) content, as measured by headspace gas chromatography-mass spectrometry (GC-MS) at 33° C., of less than 10 ppm of the one or more organic carboxylester and more than 50 ppm of the one or more mono-alcohol.

The invention also provides a method for providing low odor aqueous coating compositions, the method comprising: a) preparing one or more emulsion-polymerized addition polymer having residual organic carboxylester(s) and mono-alcohol(s); b) preparing an aqueous coating composition comprising the one or more emulsion-polymerized addition polymer; c) contacting said one or more emulsion-polymerized addition polymer, either before or after step (b), with an effective amount of one or more carboxylesterase enzyme to reduce the organic carboxylester content such that the aqueous coating composition has a headspace VOC content, as measured by headspace gas chromatography-mass spectrometry (GC-MS) at 33° C., of less than 10 ppm of the organic carboxylester and more than 50 ppm of the mono-alcohol, and such that the carboxylesterase enzyme has an ester hydrolysis activity of less than 0.03 micromole/minute in the coating composition, preferably less than 0.02 micromole/minute.

DETAILED DESCRIPTION OF THE INVENTION

Unless otherwise indicated, conditions of temperature and pressure are room temperature and standard pressure. The term "ambient cure" means cure under ambient conditions (that is, without heating). The coatings may be dried under conditions other than ambient conditions.

As used herein, unless otherwise indicated, the term "normal boiling point" refers to the boiling point of a liquid at 760 mm/Hg.

Unless otherwise indicated, any term containing parentheses refers, alternatively, to the whole term as if no parentheses were present and the term without that contained in the parentheses, and combinations of each alternative. Thus, the term "(meth)acrylate" means acrylate, methacrylate, or mixtures thereof, and, similarly, the term "(meth)acrylic" refers to any of acrylic, methacrylic, and mixtures thereof.

As used herein, the term "polymer" includes the term "copolymer", and, unless otherwise indicated, the term "copolymer" refers to polymers made from any two or more different monomers, e.g. terpolymers, pentapolymers etc., and homopolymers functionalized after polymerization so that two or more different functional groups are present in the product copolymer.

As used herein, unless otherwise indicated, the term "emulsion polymer" refers to a polymer made by emulsion polymerization. An "acrylic emulsion polymer" herein means an emulsion polymer comprising at least 50% by weight of polymerized units of ethylenically unsaturated (meth)acrylates. A "styrene-acrylic emulsion polymer" is an emulsion polymer comprising at least 50% by weight of polymerized units which are derived from either ethylenically unsaturated (meth)acrylates or styrene, and wherein the polymer comprises at least 5% of each of these types of polymerized unit. Similarly, a "vinyl acetate-acrylic emulsion polymer" is an emulsion polymer comprising at least 50% by weight of polymerized units which are derived from either ethylenically unsaturated (meth)acrylates or vinyl acetate, and wherein the polymer comprises at least 5% of each of these types of polymerized unit. A "vinyl acetate-ethylene emulsion polymer" is similarly defined.

As used herein, the term "naturally derived plasticizer" refers to animal-derived oil, fish-derived oil, plant-derived oil, alkyl esters thereof, glycerides thereof, and mixtures thereof.

As used herein, the phrase "glass transition temperature" or "Tg" refers to a measured Tg, determined by differential scanning calorimetry (DSC) using a heating rate of 10° C./minute, taking the mid-point in the heat flow versus temperature transition as the Tg value.

As used herein, unless otherwise indicated, the term "molecular weight" when referring to (co)polymers means the weight average molecular weight of a (co)polymer as measured by gel permeation chromatography (GPC), as calibrated with a polystyrene standard. Gel permeation chromatography separates the members of a distribution of polymer chains according to their hydrodynamic size in solution rather than their molar mass. The system is then calibrated with standards of known molecular weight and composition to correlate elution time with molecular weight. The techniques of GPC are discussed in detail in Modern Size Exclusion Chromatography, W. W. Yau, J. J Kirkland, D. D. Bly; Wiley-Interscience, 1979, and in A Guide to Materials Characterization and Chemical Analysis, J. P. Sibilia; VCH, 1988, p. 81-84.

Small molecule compounds, as opposed to polymers, have a fixed molecular structure and do not require averaging techniques in describing a molecular weight. Herein, the molecular weight of small molecule compounds, which latter include the volatile organic compounds that are the source of odor in coating compositions and paint compositions, are described by the formula molecular weight (the sum of the atomic masses of the constituent atoms of the molecular formula). These can be determined accurately by mass spectrometry using appropriate standards as known in the art.

Volatile organic compounds (VOCs) are the cause of odor in coating compositions. A VOC is defined herein as a carbon containing compound that has a boiling point below 270° C. at atmospheric pressure. Compounds such as water and ammonia are excluded from VOCs (although use of ammonia should be avoided or at least minimized for these low odor compositions). Regulations to minimize VOCs in coatings compositions target the total amount of such compounds in the composition, referred to herein as "bulk VOCs". Measurement of bulk VOCs and detection of specific entities in the bulk usually involves sampling the headspace of compositions subjected to 130-150° C. heat. In sampling for VOCs that may be the source of odor generated under ambient conditions of use, detection of odor-causing VOCs is conducted under conditions of 33° C. and samples are taken from the headspace volume of the container, as described in Example 1. VOCs detected under these conditions are referred to herein as "headspace" VOCs.

By "organic carboxylester" herein is meant an organic molecule wherein at least one ester grouping, —COOR, is present, wherein R is a radical composed of carbon and hydrogen atoms such as, for example, alkyl, branched alkyl, alkenyl, and vinyl. Excluded are R groups bearing polar-hetero atoms such as, for example, 2-hydroxyethyl methacrylate. Measurement of the headspace VOC content of organic carboxylesters is described in Example 1.

Carboxylesterase as used herein is defined as an enzyme of Group EC 3.1.1, excluding sub-class EC 3.1.1.1 (non-specific substrates), as classified by the Nomenclature Committee of the International Union of Biochemistry. The sub-class EC 3.1.1.1, which is excluded, includes pig liver esterase (PLE). Enzyme activity and the method of measuring enzyme activity are described in Example 2. The ester hydrolysis activity of the composition is determined at a time period between 1 week and 3 months after forming the composition.

A coalescing agent is a compound that is added to a waterborne emulsion polymer, paint, or coating, which reduces the minimum film forming temperature (MFFT) of the emulsion polymer, paint or coating by at least 1° C. The MFFT is measured using ASTM test method D2354. A non-VOC coalescing agent is a coalescing agent which has a boiling point above 270° C. at atmospheric pressure.

"KU viscosity" is a measure of the mid-shear viscosity as measured by a Krebs viscometer. The Krebs viscometer is a rotating paddle viscometer that is compliant with ASTM-D562. KU viscosity was measured on a Brookfield Krebs Unit Viscometer KU-1+ available from Brookfield Engineering Labs (Middleboro, Mass., USA). "KU" shall mean Krebs unit.

A stable low odor aqueous coating composition has a stable rheology profile as measured by change in KU viscosity, "delta KU" (change measured from an initial KU viscosity determined 1 day after formulating the coating composition); that is, the composition displays a delta KU of less than 8 KU over a 1 week period at room temperature (23° C.), and a delta KU of less than 10 KU over a 10 day period at 50° C.

The singular forms "a," "an," and "the" include plural referents unless the context clearly dictates otherwise. The endpoints of all ranges directed to the same component or property are inclusive of the endpoint and independently combinable.

This invention provides stable low odor coating compositions and low odor paints. One source of the odor in waterborne paints results from the residual organic carboxylester compounds remaining from formation of the emulsion polymer, which functions as the binder in the coating composition.

Emulsion-polymerized addition polymers which function as binders in the practice of this invention may be prepared by one of many techniques well-known in the art. At least one ethylenically-unsaturated monomer is used to prepare the emulsion-polymerized addition polymer used in the low odor coatings of this invention. For example, acrylic ester monomers including methyl (meth)acrylate, ethyl (meth)acrylate, butyl (meth)acrylate, 2-ethylhexyl (meth)acrylate, decyl (meth)acrylate, isodecyl (meth)acrylate, hydroxyethyl (meth)acrylate, and hydroxypropyl (meth)acrylate, and other $C_1$-$C_{40}$ alkyl (meth)acrylates; acid monomers, in either the acid or anionic form, such as (meth)acrylic acid, itaconic acid, and other ethylenically unsaturated carboxylic acid monomers, as well as strong acid sulfur-containing or phosphorus-containing monomers; amino-functional monomers such as, for example, N,N-dimethylaminoethyl (meth)acrylate; (meth)acrylamide or substituted (meth)acrylamides such as, for example, N-methylol(meth)acrylamide; styrene or substituted styrenes; butadiene; ethylene; vinyl acetate or other vinyl esters; vinyl ethers; (meth)acrylonitrile; and the like, may be used. Low levels of multi-ethylenically unsaturated monomers such as, for example, allyl methacrylate, diallyl phthalate, 1,4-butylene glycol dimethacrylate, 1,6-hexanedioldiacrylate, may be used.

In an embodiment, the emulsion-polymerized addition polymer comprises polymerized units of ethylenically unsaturated monomers suitable for effecting ambient cure. Accordingly, the emulsion-polymerized addition polymer may comprise polymerized units of a carbonyl containing monoethylenically unsaturated monomer. Examples of suitable unsaturated monomers which bear carbonyl functional groups include acetoacetoxyethyl(meth)acrylate, (meth)acrolein, diacetone-acrylamide, crotonaldehyde, 4-vinylbenzaldehyde, vinyl alkyl ketones of 4 to 7 carbon atoms such as vinyl methyl ketone, and (meth)acryloxy-alkyl propanols. Further suitable examples include (meth)acrylamidopivalaldehyde, 3-(meth)acrylamidomethylanisaldehyde, and diacetone (meth)acrylate. A carbonyl containing monomer may be sufficient to effect an ambient cure, however, advantageously, in an embodiment the coating composition further comprises a polyamine or polyhydrazide to effect an ambient cure. Suitable polyamines include, but are not limited to, those with 2 to 10 functional groups per molecule. Suitable examples include ethylene diamine, 4-amino-1,8-octanediaminopropylene diamine, decamethylene diamine, 1,2-diaminocyclohexane, isophorone diamine, urea, melamine, N-(2-hydroxyethyl)ethylene diamine, tris(2-aminoethyl) amine, diethylene triamine, dipropylene triamine, dibutylene triamine and polyethylene imines. Suitable polyhydrazides may include oxalic acid dihydrazide, malonic acid dihydrazide, succinic acid diyhydrazide, adipic acid dihydrazide, sebacic acid dihydrazide, cyclohexane dicarboxylic acid dihydrazides, azelaic bisdihydrazide; also carbonic acid hydrazides, bis-semicarbazides, trihydrazides, dihydrazidoalkones and dihydrazides of aromatic hydrocarbons, such as, for example 1,4-dihydrazinobenzine and 2,3-dihydrazinonaphthalene, dihydrazine.

In an embodiment, the one or more emulsion-polymerized addition polymer comprises an acrylic, styrene-acrylic, vinyl acetate-acrylic or vinyl acetate-ethylene emulsion polymer in an amount of at least 5% by weight of the emulsion polymer solids on total coating composition solids. In another embodiment, the one or more emulsion-polymerized addition polymer comprises an acrylic, styrene-acrylic or vinyl acetate-acrylic emulsion polymer in an amount of at least 10%, or at least 20%, by weight of the emulsion polymer solids on total coating composition solids.

Anionic, cationic, or nonionic surfactants, or suitable mixtures thereof, may be used to prepare the emulsion-polymerized addition polymer. The polymerization may be carried out by various means such as, for example, with all of the monomer in the reaction kettle at the beginning of the polymerization reaction, with a portion of the monomer in emulsified form present in the reaction kettle at the beginning of the polymerization reaction, and with a small particle size emulsion polymer seed present in the reaction kettle at the beginning of the polymerization reaction. The polymerization reaction may be initiated by various methods known in the art such as, for example, by using the thermal decomposition of an initiator or by using an oxidation-reduction reaction ("redox reaction") to generate free radicals in order to effect the polymerization. The molecular weight of the emulsion polymer may be greater than 1,000,000.

Chain transfer agents including mercaptans, polymercaptans, and halogen compounds may be used in the polymerization mixture in order to moderate the molecular weight of the emulsion-polymerized addition polymer as known in the art. In the art, the more hydrophobic mercaptans tend to be favored because they tend to associate with the hydrophobic polymer particle as opposed to the aqueous phase. As a result, they tend to be less volatile and less odorous than the more hydrophilic mercaptans, such as methyl mercaptopropionate (MMP) and butyl mercaptopropionate (BMP). The latter are often avoided because they tend to stay with the aqueous phase and are more volatile and odorous. However, odor from MMP and BMP are significantly reduced in the inventive compositions because these esters, if unreacted, are hydrolysed by the carboxylesterase, so these mercaptans may also be useful. The molecular weight of the emulsion polymer may be in the range of from 20,000 to 5,000,000. In one embodiment, the molecular weight of the emulsion polymer ranges from 100,000 to 1,000,000; in another embodiment, the molecular weight of the emulsion polymer ranges from 100,000 to 500,000.

The polymerization reaction may be carried out in a multistage process; the particles resulting from such a process may comprise at least two mutually incompatible polymers such as, for example, in core-shell structured particles and other known morphologies as known in the art.

The particle size of the emulsion polymer particles may be in the range of about 40 nanometers to about 5000 nanometers. However, bimodal and polymodal particle size distributions may be employed.

In most cases the emulsion-polymerized addition polymerization will not proceed to the point of 100% conversion of the ethylenically unsaturated monomer to polymer within a reasonable time. Subsequent conversion of the remaining ethylenically-unsaturated monomer to polymer by methods such as, for example, heating for prolonged periods, with or without the addition of an ion or a free radical source; removal of organic esters by methods such as, for example, adsorption, vacuum stripping, steam sparging; or conversion to a nonvolatile adduct have all been disclosed and may, where suitable, be utilized prior to, during, or after effecting the method of this invention.

For the inventive coating and paint compositions, reduced levels of the carboxylester compounds may be achieved by contacting either the coating formulation or the constituent emulsion polymer latex with a carboxylesterase. Organic carboxylester compounds that may be lessened include ethylenically-unsaturated organic carboxylester compounds such as, for example, ethyl acrylate, alkyl (meth)acrylates, dimethyl itaconate, vinyl acetate, and diallyl phthalate, and may also include organic carboxylester compounds which are not ethylenically-unsaturated such as, for example, ethyl acetate, butyl acetate, butyl propionate, methyl isobutyrate, and the like. Preferred organic carboxylesters to be reduced are C1-C8 alkyl (meth)acrylates and vinyl acetate.

Coating compositions and paints comprising the emulsion-polymerized addition polymer may contain, in addition, other components such as, for example, other polymers or emulsion-polymerized addition polymers, surfactants, emulsifiers, pigments, fillers, extenders, dispersants, anti-migration aids, curing agents, coalescents, wetting agents, preservatives, biocides, mildewcides, plasticizers, anti-foaming agents, defoamers, colorants, dyes, pearlescents, adhesion promoters, waxes, leveling agents, optical brighteners, ultraviolet stabilizers, rheology modifiers, anti-oxidants, or crosslinkers. In order to utilize such components and have them function in a manner consistent with their intended use, it is important that any added enzyme does not degrade these components. Accordingly, enzyme type, selectivity and concentration must be carefully controlled.

Low odor coatings and paints are obtained by reducing the carboxylester content of the composition. The latter derives primarily from the emulsion polymerization reaction to produce the binder. The reduction of the organic carboxylester content is achieved by treating either the aqueous emulsion polymer latex or the coating composition with a hydrolase. Specifically, these hydrolases are carboxylic ester hydrolases, generally referred to herein as carboxylesterases, and are classified as EC 3.1.1. These enzymes use water in a chemical reaction to cleave an ester bond, producing an alcohol and an acid. Carboxylesterases that may be suitable to treat the polymer or coating composition include, but are not limited to, any enzyme referred to as an esterase, carboxylesterase or lipase. The origin of the carboxylesterase may be animal, vegetable or microbial. Known sources of carboxylesterase enzyme include organisms composed of eukaryotic cells, i.e., cells with nucleii, such as, for example, animal tissues, plants, molds, and yeast. Carboxylesterases which may be suitable, for example, include those present in *Aspergillus* sp., *rhizoctonia* s., *tricoderma* h., *cytophagia* sp., yeast, bovine liver, sheep liver, chicken liver, and the like. Although carboxylesterase enzymes are found in nature such as, for example, in the species disclosed herein-above, recently developed methods may allow the transfer of the carboxylesterase gene to bacteria to facilitate the production of carboxylesterase enzymes, as disclosed in J. Sambrook, et al., "Molecular Cloning: A Laboratory Manual", Second Edition, Cold Spring Harbor Laboratory Press, Plainview, N.Y., 1989. Accordingly, genetically or chemically modified variants of carboxylic ester hydrolases may be suitable. Also included are carboxylesterases that are expressed in an organism other than the original source organism.

The enzyme may be used in solution or immobilized; preferably, the enzyme is soluble in the aqueous coating composition. Preferred esterases are microbial in origin and include the fungal enzyme cutin hydrolase (cutinase) as well as those obtained directly from, or derived from, *Candida antarctica* and *Thermomyces lanuginosus*. Potentially useful commercial preparations include Novozym™ 435, Lipex™ 100L, Novozym™ CALB L and Novozym™ 51032 (Novozymes, Bagsvaerd, Denmark), generic CALB (Chiralvision, Leiden, The Netherlands), Lipase G Amano 50 (Amano Enzyme, Nagoya, Japan) and Lipase R (Deerland, Kennesaw, Ga.). Preferred commercial preparations are generic CALB, Novozym™ CALB L, and Novozym™ 51032. The carboxylesterase of use must be chosen and dosed based on tests in specific latex formulations that indicate hydrolysis of residual esters but no damage to the formulation. Some enzymes are not useful for the present invention because they lack specificity or are so aggressive in effecting hydrolysis of esters that they cause damage to the paint components at any enzyme usage level which is effective in reducing carboxylester levels. One such unsuitable enzyme is pig liver esterase (PLE), which has been found to have a severely deleterious effect on a number of coatings properties when used at any enzyme usage level which is effective in reducing carboxylester levels. PLE fails to achieve the combined goal of reduced levels of the odorous carboxylesters in aqueous coating compositions while at the same time providing stable coating formulations. Accordingly, the low odor coating compositions do not comprise PLE.

The carboxylesterase must be present in a sufficient amount to be effective in reducing the organic carboxylester content of the aqueous coating composition. However, as alluded to above, there is a practical upper limit of use for the majority of these enzymes due to the undesirable reactivity with the coating formulation components. In particular, coatings manufacturers require viscosity stability in the aqueous coating composition. Preferably, the composition displays a delta KU of less than 10, more preferably less than 8, and even more preferably less than 5 KU over a 1 week period at room temperature; and a delta KU of less than 15, more preferably less than 10, and even more preferably less than 5 KU over a 10 day period at 50° C. Deterioration of key properties of the coating resulting from addition of the carboxylesterase enzyme is also indicative of an unstable aqueous coating composition. For a stable aqueous coating composition, preferably the coating has a 1 day room temperature block resistance of at least 6, and a 1 day hot block resistance of at least 6. For a stable aqueous coating composition, preferably the scrub resistance of the coating is not more than 10% lower than the analogous coating formulation which does not comprise the carboxylesterase enzyme. Similarly, an increased coalescent demand in order to achieve film formation for the enzyme-containing composition is indicative of an unstable composition; that is, reaction of the enzyme with the coalescent renders the latter ineffective in achieving film formation.

Moreover, the preferred quantity of carboxylesterase depends on the enzyme type and source, including the purity, of the enzyme. The amount of carboxylesterase which is used is preferably in the range of from about 0.1 ppm, or from 0.25 ppm, or more preferably from 1 ppm, up to about 20 ppm, more preferably up to 10 ppm, even more preferably up to 5 ppm, and still more preferably up to 3 ppm by solid weight of enzyme based on the weight of the aqueous coating composition. Because the enzyme source and purity can affect the preferred quantity of enzyme, a useful way to quantify the enzyme is by enzyme carboxylester hydrolysis activity, referred to herein as enzyme activity. In order to prevent degradation of the paint formulation components, the carboxylesterase ester hydrolysis activity should be less than 0.03, and preferably less than 0.02, micromoles per minute.

The carboxylesterase is believed to catalyze the hydrolysis of a carboxylic ester to yield an alcohol and a carboxylic acid anion. The alcohol and carboxylic acid compounds are less odorous in a coating composition than are their carboxylic ester compound analogs. Reduction of carboxylester content in the coating composition upon carboxylesterase treatment is therefore accompanied by an increase in the corresponding alcohol content. Preferably, the aqueous coating composition has a headspace VOC content, as measured by headspace GC-MS at 33° C., of less than 15 ppm, preferably less than 10 ppm, more preferably less than 8 ppm, and even more preferably less than 5 ppm, and still more preferably less than 2 ppm of organic carboxylesters having a boiling point of less than 150° C.; and headspace VOC levels of more than 50 ppm of monoalcohol with a formula molecular weight of less than 76.

The emulsion-polymerized addition polymer may be contacted by the carboxylesterase in any convenient manner such as, for example, by admixing a carboxylesterase with an emulsion-polymerized addition polymer in an emulsion reaction kettle, or by post-addition of the enzyme to the isolated emulsion polymer latex, or by passing the emulsion-polymerized addition polymer through a column packed with a carboxylesterase immobilized on a solid support such as, for example, a carboxylesterase immobilized on acrylic beads. Alternatively, the carboxylesterase may be post-added to the coating composition comprising the emulsion-polymerized addition polymer, or the coating composition may be passed through a column packed with the immobilized enzyme. The contacting step may take place at pH greater than about 4. Preferred is a pH greater than about 7, and a pH greater than 8 is more preferred. The contacting step may take place at a temperature of from about 15° C. to about 95° C. Preferred is a temperature of from about 25° C. to about 65° C.

Conventional methods of VOC reduction may be combined with the enzyme treatment. For example, steam stripping actually becomes more effective in combination with enzyme treatment (see Example 9).

The aqueous coating composition optionally contains inorganic particles. A suitable range for the amount of inorganic particles included in the aqueous coating composition is from 0 to 95 volume %, based on the total dry volume of the aqueous composition and inorganic particles. Typically, the aqueous coating composition of this invention, when used to prepare dried coatings, has a solids level in the range of from 20 to 50 volume %, based on the volume of the aqueous coating composition. The pH of the aqueous coating composition is typically in the range of from 3 to 11, and preferably, in the range of from 7 to 10. A suitable viscosity range for the aqueous coating composition is from 50 to 130 Kreb units (KU), preferably from 70 to 110 KU, and more preferably from 90 to 100 KU.

Inorganic particles include: inorganic pigments; metal oxides such as zinc oxide, antimony oxide, zirconium oxide, chromium oxide, iron oxide, lead oxide, aluminum oxide, silicon oxide, titanium dioxide; zinc sulfide, lithopone, calcium carbonate, calcium sulfate, barium sulfate, mica, clay, calcined clay, feldspar, nepheline syenite, wollastonite, diatomaceous earth, alumina silicates, and talc. In one embodiment the inorganic particles may have a particle size which is less than 100 nm. Examples of desired inorganic particles with a particles size of less than 100 nm include silicon oxide, titanium dioxide, and iron oxide.

The aqueous coating composition may optionally contain organic pigment particles. Suitable organic pigments also include plastic pigments such as solid bead pigments and microsphere pigments containing voids or vesicles. Examples of solid bead pigments include polystyrene and polyvinyl chloride beads. Examples of microsphere pigments include polymer particles containing one or more voids such as Ropaque™ opaque polymers (The Dow Chemical Company, Midland, Mich.) and vesiculated polymer particle, as known in the art. Other known pigments and fillers may be used.

Conventionally, the aqueous coating compositions contain one or more volatile organic compounds ("VOC"). A VOC is defined herein as a carbon containing compound that has a boiling point below 270° C. at atmospheric pressure. Frequently a VOC is deliberately added to a paint or coating to improve the film properties of a coating or to aid in the application properties of the composition employed to prepare the coating. Examples are glycol ethers, organic esters, aromatic compounds, ethylene and propylene glycol, and aliphatic hydrocarbons.

The aqueous coating compositions of this invention optionally contain organic solvents, coalescents, or plasticizers, which may or may not be VOCs. These may be ester compounds that aid in the film forming properties of the aqueous coating composition to achieve desirable properties. These properties include but are not limited to coalescing of the particles of film-forming polymer at temperatures below the glass transition temperature of the polymers; resistance to gelation of the composition during repeated cycles of freezing and thawing; and the adhesion, leveling, toolability, wet-edge and gloss development, and resistance to scrubbing and organic solvents exhibited by coatings and paints applied using the compositions. Conventional coalescents are typically volatile liquid organic compounds including but not limited to dihydric alcohols, glycols, oligomeric glycols, esters of alcohols and glycols, and ethers.

However, due to odor and health and environmental concerns, many national and regional governments have issued restrictions concerning the amounts of volatile organic compounds (VOCs) that can be present in compositions intended for use as coatings, inks, sealants, adhesives and related applications (i.e. bulk VOCs). These restrictions have initiated efforts by manufacturers and formulators of these compositions to seek ways to eliminate or at least reduce the concentration of bulk VOCs in aqueous polymer compositions without adversely affecting the beneficial properties imparted by these compounds. Accordingly, it is preferable that the solvents, coalescents, or plasticizers do not contribute to the coating's bulk VOC content.

In one embodiment, the aqueous coating composition contains up to 20 wt. % bulk VOC based on the total weight of the aqueous coating composition; preferably less than 5 wt. % VOC, more preferably less than 3 wt. % VOC, and even more preferably, less than 1.7 wt. % VOC based on the total weight of the aqueous coating composition.

Typical methods of paint or coating preparation introduce adventitious VOCs from the preparation of the aqueous composition, such as via biocides, defoamers, soaps, dispersants, and thickeners. These typically account for 0.1% bulk VOC by weight based on the total weight of the aqueous coating composition. Additional methods such as steam stripping and choice of low VOC containing additives like biocides, defoamers, soaps, dispersants, and thickeners are suitable for further reducing the aqueous coating composition to less than 0.01% VOC by weight based on the total weight of the aqueous coating composition. In one embodiment, the aqueous coating composition has a bulk VOC, by weight based on the total weight of the aqueous coating composition, of less than 0.1% (1,000 ppm); more preferably, the aqueous coating composition has a bulk VOC of less than 0.07% (700 ppm), even more preferably less than 0.01% (100 ppm).

In another embodiment, the low VOC aqueous coating composition may contain one or more coalescing agent that is not a VOC, such as, for example, plasticizers, low molecular weight polymers, surfactants, and autooxidizable plasticizers such as alkyl esters of unsaturated fatty acids, including mono, di-, or tri-unsaturated fatty acids. Preferred are naturally derived plasticizers, including, for example, alkyl esters prepared from oils such as linseed, tung, dehydrated castor, soybean, tall, sunflower, and corn. Suitable unsaturated fatty acid esters include monounsaturated fatty acid esters formed from palmitoleic acid, oleic acid, or caproleic acid; diunsaturated fatty acid esters formed from linoleic acid; triunsaturated fatty acid esters formed from linolenic acid or eleosteric acid, or mixtures thereof. Suitable esters of unsaturated fatty acids includes alkyl esters, such as methyl and ethyl esters; substituted alkyl esters, such as esters formed from ethylene glycol and propylene glycol; and alkyl ether esters of unsaturated fatty acids, diethylene glycol, triethylene glycol, dipropylene glycol, tripropylene glycol, and diethylene glycol monobutyl ether. In one embodiment, the above auto autooxidizable plasticizers are used in conjunction with an emulsion polymer comprising 0.25% to 12.5% of acetoacetoxyethyl (meth)acrylate as polymerized units. Auto oxidation can further be enhanced by the use of metal ion catalysts such as cobalt, zirconium, calcium, manganese, copper, zinc and iron. Simple salts such as halides, nitrates, and sulfates may be used but in many cases an organic anion such as the acetate, naphthenate or acetoacetonate is used.

In a particularly preferred embodiment, the emulsion polymerized addition polymer is formed and subsequently contacted with the carboxylesterase (5 ppm of Novozym 51032, based on parts of solid enzyme in the total aqueous composition) after a redox pair has been added to reduce the level of residual monomer and while the material is still at an elevated temperature. Alternatively, the enzyme can be added during or before addition of the redox pair without loss of activity. Preferably the pH is >3.5. The material is allowed to cool while ester levels continue to drop. The material may be formulated, either before, or after, stabilization of the residual ester levels, to produce a low odor, low VOC, paint.

Also provided is a method for providing these low odor aqueous coating compositions, the method comprising: a) preparing one or more emulsion-polymerized addition polymer having residual organic carboxylester(s) and mono-alcohol(s); b) preparing an aqueous coating composition comprising the one or more emulsion-polymerized addition polymer; c) contacting the one or more emulsion-polymerized addition polymer, either before or after step (b), with an effective amount of one or more carboxylesterase enzyme to reduce the organic carboxylester content such that the aqueous coating composition has a headspace VOC content, as measured by headspace gas chromatography-mass spectrometry (GC-MS) at 33° C., of less than 10 ppm, preferably less than 5 ppm, of the organic carboxylester and more than 50 ppm of the mono-alcohol, and such that the carboxylesterase enzyme has an ester hydrolysis activity of less than 0.03 micromole/minute in the coating composition, preferably less than 0.02 micromole/minute.

In an embodiment, the method further comprises the step of steam stripping at any time after step (a) to aid in removal of VOCs.

In another embodiment of the method, the one or more emulsion-polymerized addition polymer comprises an acrylic, styrene-acrylic, vinyl acetate-acrylic or vinyl acetate-ethylene emulsion polymer in an amount of at least 5%, preferably at least 10%, or at least 20%, by weight of the emulsion polymer solids on total coating composition solids.

In a different embodiment of the method, the one or more emulsion-polymerized addition polymer comprises polymerized units of a carbonyl containing monethylenically unsaturated monomer, and, optionally, the composition further comprises a polyamine or polyhydrazide.

Preferably, compositions made by these methods have a bulk VOC of less than 1,000 ppm, more preferably less than 700 ppm, and even more preferably less than 100 ppm.

Conventional coatings application methods such as, for example, brushing, rolling, and spraying methods such as, for example, air-atomized spray, air-assisted spray, airless spray, high volume low pressure spray, and air-assisted airless spray may be used to apply the aqueous polymer composition of this invention. Additionally, for some systems, other application techniques may be used to apply the aqueous polymer composition, such as, caulk gun, roll coaters, and curtain coaters. The aqueous polymer composition may be advantageously applied to substrates such as, for example, plastic, wood, metal, primed surfaces, previously painted surfaces, weathered painted surfaces, glass, composites, and cementitious substrates. Drying is typically allowed to proceed under ambient conditions such as, for example, at 0° C. to 35° C. but may be accelerated with heat or low humidity.

EXAMPLES

Materials and Abbreviations

Enzymes:

CALBL is Novozym™ CALB L [Novozymes, Bagsvaerd, Denmark], supplied as a 6% solution. N51032 is Novozym™ 51032 [Novozymes, Bagsvaerd, Denmark], supplied as a 5% solution. Lipex is Lipex™ 100L [Novozymes, Bagsvaerd, Denmark], supplied as a 7% solution. PLE is Pig Liver Esterase [Sigma Aldrich, St. Louis, Mo.], supplied as a 1.6% solution. *Candida* is *Candida Cylindracea* [Sigma Aldrich, St. Louis, Mo.], used as a 5% solution.

Formulation Components:

Rhoplex™ AC-261 [The Dow Chemical Company, Midland, Mich.]

Rhoplex™ VSR-2015 [The Dow Chemical Company, Midland, Mich.]

Ropaque™ Ultra E [The Dow Chemical Company, Midland, Mich.]

Ropaque™ Ultra [The Dow Chemical Company, Midland, Mich.]

Acrysol™ RM-3000 [The Dow Chemical Company, Midland, Mich.]

Acrysol™ RM-895 [The Dow Chemical Company, Midland, Mich.]

Acrysol™ RM-5 [The Dow Chemical Company, Midland, Mich.]

Tamol™ 731A [The Dow Chemical Company, Midland, Mich.]

Tergitol™ 15-S-20 (80% Aqueous) [The Dow Chemical Company, Midland, Mich.]

BYK™-024 [Byk-chemie GmbH, Wesel, Germany]

Foamstar™ A-34 [Cognis, Cincinnati, Ohio]

Texanol™ [Eastman Chemical, Kingsport, Tenn.]

Tioxide™ RTC-90 [Huntsman, Billingham, UK]

Kronos™ 4311 [Kronos Worldwide Inc, Dallas, N.J.]

Minex™ 10 [Unimin, New Canaan, Conn.]
Satintone™ 5HB [BASF, Ludwigshafen, Germany]
Durcal™ 2 [Omya, Alpharetta, Ga.]
Attagel™ 50 [BASF, Ludwigshafen, Germany]
Natrosol™ Plus 330 [Hercules, Wilmington, Del.]
Natrosol™ 250 MHR [Hercules, Wilmington, Del.]
HEC is hydroxy ethyl cellulose
HEUR is hydrophobically modified urethane rheology modifier
EA is ethyl acrylate
BA is butyl acrylate
EHA is ethylhexyl acrylate
MMA is methyl methacrylate
Sty is styrene
VAc is vinyl Acetate
GC is gas chromatography
FID is flame ionization detection
MS is mass spectrometry Test Procedures The following test procedures were used to generate the data reported in the Examples.

Scrub Resistance Test

This test (based on ASTM D 2486-06) was performed as follows:

A. Preparation of Apparatus:
1. Abrasion Tester—An abrasion testing device is used which consists of a brush clamped into a bracket which is moved back and forth over the dried, applied paint film by means of a set of cables on either side. The abrasion tester must be leveled before use and operated at 37±1 cycles/minute.
2. Brush—The bristles, if new, must be leveled before use to permit uniform wear on the paint surface. Leveling is accomplished by running the brush over 100 or 120 mesh aluminum oxide close grain sandpaper.

B. Test:
1. Draw down the paint on a black vinyl chart (Type P-121-10N, The Leneta Company) using the 7 mil opening of a 7/10 Dow film caster, starting from the secured end of the panel. The time for application should be fairly slow, 3 to 4 seconds from end to end, to prevent formation of pinholes in the film. Air dry in a horizontal position for 7 days in an open room kept at 73.5+/−3.5° F. and 50+/−5% relative humidity.
2. Make three drawdowns of each sample. Test two and average them if they are within 25% repeatability. If they are not, test a third and average the three.
3. Secure the drawdown to the abrasion tester by using a gasketed frame and brass weights or clamps.
4. Mount the brush in the holder. Dispense 10 grams of a scrub medium (Abrasive Scrub Medium, Type SC-2, The Leneta Company) onto the secured drawdown. Place the brush at the center of the path before starting the test.
5. Start the test. After each 400 cycles before failure, an additional 10 g of stirred scrub medium is dispensed onto the chart.
6. Record the number of cycles to remove the paint film fully in one continuous line.

Peel Block Resistance Test

This test is based on ASTM Test Method D 4946-89. Films were drawn down as follows: 8 to 10 ml of the paint was transferred on to the test chart (Leneta Charts) in front of the drawdown bar (3 Mil Bird Film Applicator). Immediately, grasping the drawdown bar with both hands, a smooth film was drawn over the test paint at a rate of about 6 cm per sec (5 sec per test chart). The films were cured in a constant temperature room (CTR) for a specified period of time (1 day or 7 days) depending on the test requirement. Four 4 cm×4 cm sections (to run duplicates) of each type of paint film were prepared. The cut sections were placed with the paint surfaces face to face and then placed on a flat metal plate. Each individual specimen was topped with a number 8 rubber stopper, with narrow side down, and a 1000 g. weight was placed on each stopper. It is desirable to rate the block resistance of each paint under 2 sets of conditions. These are for face-to-face contact for: (i) 24 hours at room temperature, and (ii) 30 minutes at 50° C. In all cases, the weights and stoppers were equilibrated under the test conditions. After the test period, the stoppers and weights were removed and the sections separated with slow and steady force at an angle of approximately 180°. The samples were then rated for block resistance on a scale of 0 to 10 as described below:

10 = no tack, perfect
9 = trace tack, excellent
8 = slight tack, very good
7 = slight tack, good
6 = moderate tack, good
5 = moderate tack, fair
4 = severe tack, no seal, fair
3 = 5-25% seal, poor
2 = 25-50% seal, poor
1 = 50-75% seal, poor
0 = complete seal, very poor tack This invention provides low odor coating compositions and paints. The examples illustrate how stable low odor aqueous paints may be obtained, although they are not intended to limit the invention.

Example 1

Determination of Headspace VOC Content—Based on ASTM D3960-05

Headspace VOC content in aqueous compositions was determined by a method based on ASTM 3960: Standard Practice for Determining Volatile Organic Compound (VOC) Content of Paints and Related Coatings. This method uses static headspace sampling/GC-MS at 33° C. to determine the headspace concentrations of compounds above aqueous emulsion polymers or waterborne paints.

Preparation of Standards:

Prepare Calibration Standards in Appropriate Solvent (e.g. Thf) containing each compound to be calibrated at a minimum of three concentrations. Standard concentrations should be prepared by serial dilution and calculated in parts-per-million (ppm) on a weight/weight basis. The concentration of each compound in the lower and higher concentration standards should generate a detector response that brackets the response of the compound as determined in the analysis of the sample. Weigh 20 mg of each standard into 22 ml headspace vials with aluminum caps and crimp the cap tightly. Repeat the procedure with water blanks to be run, at a minimum, at the beginning and end of a sequence of samples. Run the headspace vials containing the standards via headspace GC-MS as known in the art. For each of the compounds requiring calibration, prepare a calibration plot using the three standard concentrations for that compound. Plot the integrated area of the MS response for the compound on the Y-axis versus the concentration on the X-axis. Create a linear-least-squares fit to the calibration plot.

Sampling Procedure:

Weigh 5 g of each sample into 22 ml headspace vials with aluminum caps and crimp the cap tightly. Repeat the procedure with water blanks to be run, at a minimum, at the beginning and end of a sequence of samples. Analyze the samples via headspace GC-MS. Integrate all peaks in the resulting chromatogram that have a signal greater than five times the root-mean-square baseline noise. Once a satisfactory separation of the volatiles is achieved, mass spectral analysis and/or retention time matching against known compounds is used to identify the compounds detected. Determine the concentration of each calibrated compound in the sample headspace using the linear-least-squares equation from the calibration plot for that compound.

Example 2

Determination of Enzyme Hydrolytic Activity

The procedures to measure the enzyme activity for either an emulsion polymer latex or a latex paint are similar. In the case of an emulsion polymer latex, 100 g samples of emulsion polymer latex binder were treated with different enzymes with concentrations varying from 2.5 to 1,000 ppm (weight of solid enzyme on weight of wet latex). After equilibrating for 1 day, the samples were further treated with approximately 600 ppm of ethyl acrylate (EA), and incubated in sealed jars at pH of 8.5 and room temperature for 48 hours. 5 g samples were taken at intervals of 15, 75, 135, 1440 and 2880 minutes, diluted with 5 g of DI water, inhibited with 100 ppm of 48% phosphoric acid to a pH of approximately 1.6 and then mixed thoroughly. Catalytic activity of free enzyme was then determined by calculating changes in headspace EA for the inhibited latex samples by GC/FID (by the method of Example 1) at the interval time where approximately 10% of the EA was consumed. Enzyme activity was expressed in micromoles of EA hydrolyzed per minute (1 unit (U)=1 µmol EA/min). Results are given in Table 10. The enzyme activity in an enzyme treated paint is measured similarly, although phosphoric acid inhibition used 400 ppm of the 48% phosphoric acid solution to attain a pH of 1.6.

Example 3

Synthesis of Emulsion Polymer Latex, Polymer A

A monomer emulsion was formed from 1397 g ethyl acrylate, 386 g methyl methacrylate (as well as <2% by weight of total monomer of methacrylic acid, sodium carbonate and n-dodecylmercaptan) with 499 g DI water and 51.8 g anionic surfactant (30% active) which was emulsified with stirring. 9 g anionic surfactant (30% active) and 547 g DI water were charged to a 4 L multi-neck flask fitted with mechanical stirring. The flask contents were heated to 75° C. under nitrogen. To the stirred kettle contents were added 67 g monomer emulsion followed by 0.02 g ferrous sulfate heptahydrate and 0.02 g tetrasodium salt of ethylenediamine-tetraacetic acid in 23.5 g DI water and sodium carbonate (<0.5% based on total monomer). Polymerization was initiated by the addition of 1.2 g sodium persulfate in 36 g DI water followed by 0.6 g sodium hydrosulfite in 5 g DI water. Gradual addition of the monomer emulsion was subsequently initiated. Separate solutions of 3.8 g APS in 160 g DI water and 1 g of D-Isoascorbic acid in 160 g DI water were fed concurrently with the monomer emulsion. After half of the monomer was fed, 55 grams of a 50% solution of ureido methacrylate was added to the remainder of the monomer emulsion. Total addition time for the three feeds was 90-100 minutes. Reactor temperature was maintained at 75° C. throughout the polymerization. 32 g DI water was used to rinse the emulsion feed line to the reactor. After completion of the monomer emulsion addition, the reactor was cooled from 75° C. to 60° C. as the residual monomer was reduced by additional redox pair addition. The polymer emulsion was neutralized to pH 8 with sodium hydroxide solution. Less than 2% by weight of anionic surfactant and preservative were then added. Final particle size was 150 nm and solids content was 50%. The polymer is designated Polymer A.

Example 4

Enzyme Treatment of Emulsion Polymer Latexes

As discussed above, carboxylester compounds, resulting from the emulsion polymerization reaction to produce the binder, are a primary source of odor. Lowering the organic carboxylester content may be achieved by contacting the aqueous emulsion polymer or coating composition with a carboxylesterase enzyme. The enzyme treatment of the emulsion polymer may be performed "in-process", that is, during formation of the emulsion polymer latex as described below; or the enzyme may be post-added to the emulsion polymer latex; or, alternatively, the enzyme may be post-added directly to the formulated coating or paint composition.

Four liters of acrylic latex was prepared by emulsion polymerization in a 5 L round bottom flask, as described above. After a redox pair was added to lower residual monomer, 0.01% (wet weight on wet weight, i.e. 0.4 g wet enzyme solution on 4,000 g latex) CALB L (liquid grade, 6% active) was added to the 45° C. material. This is equivalent to 6 ppm of solid enzyme in the emulsion polymer latex. The treated latex was allowed to cool to room temperature, and neutralized to pH of 8.5 with a 5% solution of KOH. The product was then filtered through a 100 mesh screen and stored in a 4 liter container at room temperature. Samples were removed and analyzed by GC/FID (gas chromatography/flame ionization detection) for removal of esters. Although in-process addition is more convenient, post-addition of the enzyme to the emulsion polymer latex allows sampling of the latex for residual ester content both before and after treatment with the enzyme. Treatment levels were varied by the quantity of enzyme solution added. Results are given in Table 1.

TABLE 1

Concentration of Residual Esters and Alcohols (ppm) After Enzyme Treatment Using CALBL at Various Levels for a BA/MMA Emulsion Polymer Latex [1].

| | Enzyme Treatment [2] | | | |
|---|---|---|---|---|
| | None (Control) | 6 ppm CALBL | 60 ppm CALBL | 600 ppm CALBL |
| ESTERS | | | | |
| butyl propionate | 126 | n.d. | n.d. | n.d. |
| butyl acetate | 111 | n.d. | n.d. | n.d. |
| 2-butenoic acid, butyl ester | 28 | 7 | n.d. | n.d. |
| methyl isobutyrate | 14 | 4 | n.d. | n.d. |
| butyl acrylate | 3 | n.d. | n.d. | n.d. |

TABLE 1-continued

Concentration of Residual Esters and Alcohols (ppm) After Enzyme Treatment Using CALBL at Various Levels for a BA/MMA Emulsion Polymer Latex [1].

| | Enzyme Treatment [2] | | | |
|---|---|---|---|---|
| | None (Control) | 6 ppm CALBL | 60 ppm CALBL | 600 ppm CALBL |
| ALCOHOLS | | | | |
| t-butanol | 355 | 336 | 363 | 356 |
| 1-butanol | 206 | 276 | 221 | 225 |
| Isopropanol | 173 | 174 | 192 | 181 |
| methanol | 61 | 52 | 54 | 67 |
| OTHER | | | | |
| n-butyl ether | 339 | 352 | 365 | 459 |
| acetone | 233 | 222 | 214 | 214 |
| methyl 2-hydroxyisobutyrate | 73 | 87 | 73 | 36 |
| benzaldehyde | 22 | 22 | 24 | 28 |
| propanoic acid | n.d. | 50 | 62 | 58 |
| acetic acid | n.d. | 18 | 26 | 25 |

[1] Rhoplex AC-261 ™ (Dow Advanced Materials, Philadelphia, PA) is a commercially available aqueous acrylic BA/MMA binder (other components <2%), supplied at 50% solids.
[2] Residual ester and alcohol content determined after 1 week of enzyme treatment.

Similar data was collected by the same procedure for the enzyme Novozym™ N-51032 at various enzyme levels, and shown in summary form (Table 2, below), along with that for CALBL, comparing the residual ester levels present in the latex headspace, both 1 week and 3 weeks after treatment with each enzyme.

TABLE 2

Residual Ester Content (ppm) After Various Enzyme Treatments for a BA/MMA Emulsion Polymer Latex [1].

| Enzyme | Enzyme Addition (wet on wet) | Enzyme Conc. (ppm) | Concentration of Residual Esters (ppm) Enzyme Treatment Time | |
|---|---|---|---|---|
| | | | 1 week | 3 weeks |
| Control | 0 | 0 | 282 | 282 |
| CALBL | 0.01% | 6 | 11 | 0 |
| | 0.1% | 60 | 0 | 0 |
| | 1.0% | 600 | 0 | 0 |
| N51032 | 0.001% | 0.5 | 51 | 25 |
| | 0.005% | 2.5 | 21 | 2 |
| | 0.01% | 5 | 0 | 0 |
| | 0.1% | 50 | 0 | 0 |
| | 1.0% | 500 | 0 | 0 |

[1] Rhoplex AC-261 ™ (Dow Advanced Materials, Philadelphia, PA) is a commercially available aqueous acrylic BA/MMA binder (other components <2%), supplied at 50% solids.

It can be seen that carboxylester removal is complete after three weeks even for very low levels of added enzyme, such as, for example, 6 ppm of CALBL and 5 ppm of N-51032.

Similar data was obtained for a variety of emulsion polymers to show that odor reduction can be effected for a number of polymer types, Table 3.

TABLE 3

Effect of Enzyme Treatment on Residual Ester Content (ppm) for Latexes with Different Emulsion Polymer Compositions.

| | Concentration of Residual Esters [1] (ppm) Enzyme Treatment | |
|---|---|---|
| Polymer Composition | Control (No Enzyme) | CALBL, 6 ppm |
| BA/MMA [2] | 295 | 0 |
| BA/Sty [3] | 199 | 0 |
| BA/VAc [4] | 389 | 0 |

[1] Residual ester content determined after 3 weeks of enzyme treatment (6 ppm of solids CALBL on wet latex).
[2] BA/MMA latex was Rhoplex ™ AC-261 (50% solids), as above in Tables 1 and 2.
[3] BA/Sty latex had composition: 52 BA/46 Sty/1 MAA/1 Adhesion Promoter (other components <2%; supplied at 50% solids), obtainable by the method of Example 3.
[4] BA/VAc latex was Rovace ™ 9900, a commercially available aqueous acrylic BA/VAc binder (Dow Advanced Materials, Philadelphia, PA), supplied at 55% solids.

Example 5

Effect of Enzyme Treatment of Paints on Scrub and Block Resistance

The effect of enzyme treatment on paint properties was explored in this Example by formulating enzyme-treated emulsion polymers into standard paint formulations. (Alternatively, the enzyme treatment may be effected directly by post-addition of the enzyme to the paint formulation). Some key paint properties were tested, including scrub resistance and block resistance.

Table 4, below, shows the paint formulations used to formulate paints for the scrub resistance and block resistance data presented in Tables 5 and 6, respectively.

TABLE 4

Near-Zero VOC Paint Formulations for Paints A and B

| Formulation Ingredient | Ingredient Type | Paint A Amounts (g) | Paint B Amounts (g) |
|---|---|---|---|
| Grind | | | |
| Kronos 4311 (75% solids) | TitaniumDioxide | 300.00 | 300.00 |
| Tergitol 15-S-20 (20% active) | Surfactant | 2.15 | 2.15 |

TABLE 4-continued

Near-Zero VOC Paint Formulations for Paints A and B

| Formulation Ingredient | Ingredient Type | Paint A Amounts (g) | Paint B Amounts (g) |
|---|---|---|---|
| Water | Water | 5.00 | 5.00 |
| Foamstar A-34 | Defoamer | 1.00 | 1.00 |
| Tamol 731A (25% active) | Dispersant | 5.00 | 5.00 |
| Minex 10 | Extender | 15.00 | 15.00 |
| Attagel 50 | Extender | 5.00 | 5.00 |
| Ropaque Ultra (30% active) | OpaquePolymer | 30.00 | 30.00 |
| Foamstar A-34 | Defoamer | 1.00 | 1.00 |
| Acrysol RM-3000 (20% active) | Thickener | 50.00 | 50.00 |
| LetDown | | | |
| Water | Water | 206.81 | 222.09 |
| Polymer A (50.1 % solids) [1] | Binder | 399.04 | — |
| Rhoplex VSR-2015 (49.5% solids) [2] | Binder | — | 388.76 |
| Water | Water | 15.00 | 15.00 |
| Totals: | | 1035.0 | 1040.0 |

[1] Polymer A is an aqueous acrylic binder (see Example 3).

[2] Rhoplex VSR-2015 (Dow Advanced Materials, Philadelphia, PA) is a commercially available aqueous acrylic BA/MMA binder (other components <2%).

After equilibrating overnight the paints were determined to have properties with the ranges 90<KU<100, 1.2<ICI<1.7, 8.3<pH<8.5. The paint formulations were post-treated with various levels of Lipex 100L (added as a 7% aqueous solution), stirred for 10 minutes, and then left to equilibrate overnight, prior to drawing down paint films. The results of scrub resistance tests and block resistance tests for these paints are shown in Table 5 and Table 6, respectively.

TABLE 5

Scrub Resistance[1] of Paint 'A' Post-Treated with Various Levels of Lipex 100 L.

| Enzyme Addition (wet on wet) | Enzyme Level (ppm in latex) | Enzyme Level (ppm in paint) | No. of Scrub Cycles | Scrub Cycles as % of Control |
|---|---|---|---|---|
| None | 0 | 0 | 1041 | 100% |
| 0.05% | 35 | 13.5 | 1015 | 98% |
| 0.1% | 70 | 27 | 977 | 94% |
| 0.5% | 350 | 135 | 910 | 87% |
| 1.0% | 700 | 270 | 793 | 76% |

[1] Films cured at RT (75 F.; 50% Relative Humidity) for 7 days

A reduction of 10% or more in the scrub resistance of the paint is clearly undesirable for paint manufacturers and the data indicate that levels of Lipex 100L as high as 135 ppm or 270 ppm in the paint are unacceptable. A reduction of 6% in the scrub resistance of the paint is indicative of a problem, although not conclusive.

TABLE 6

Block Resistance of Paint 'B' Post-Treated with Various Levels of Lipex 100L.

| Enzyme Addition (wet on wet) | Enzyme Level in Latex (ppm) | Enzyme Level in Paint (ppm) | 1 day hot block[1] | 1 day R/T block[2] | 7 day hot block[3] | 7 day R/T block[4] |
|---|---|---|---|---|---|---|
| None | 0 | 0 | 7 | 8 | 7 | 9 |
| 0.01% | 7 | 2.6 | 6 | 8 | 6 | 8 |
| 0.1% | 70 | 26 | 6 | 8 | 7 | 9 |
| 1.0% | 700 | 260 | 1 | 7.5 | 6 | 7 |

[1] Film cured at RT (75 F.; 50% Relative Humidity) for 1 day, block resistance measured after face-to-face contact, with applied weight, at 50° C. for 30 mins.

[2] Film cured at RT (75 F.; 50% Relative Humidity) for 1 day, block resistance measured after face-to-face contact, with applied weight, at RT for 20 hours.

[3] Film cured at RT (75 F.; 50% Relative Humidity) for 7 days, block resistance measured after face-to-face contact, with applied weight, at 50° C. for 30 mins.

[4] Film cured at RT (75 F.; 50% Relative Humidity) for 7 days, block resistance measured after face-to-face contact, with applied weight, at RT for 20 hours.

The 1-day hot block resistance is destroyed when 260 ppm of Lipex 100L is present in the paint.

Example 6

Determination of Enzyme Levels Resulting in Formulation Stability

Addition of a carboxylesterase to a paint formulation, either indirectly via addition to the emulsion polymer latex or directly by post addition to the paint, has been found to cause paint instability for some levels of carboxylesterase, which may be manifested in one or more detrimental effects on paint properties. Most commonly, the enzyme may cause viscosity instability, but loss of block resistance or loss of scrub resistance may also occur. Additionally, the enzyme may attack the coalescent, resulting in coalescent inefficiency and/or higher VOC's from the cleaved coalescent molecules.

For a given enzyme, paint formulation stability may be achieved by establishing the enzyme level at which residual enzyme activity is negligible. This was achieved as follows:

Portions of an acrylic latex binder were treated with either CALBL or N51032 at concentrations varying from 0.01 to 1% (by weight, wet on wet). The samples were split and a portion of the latex was retained as a control and another portion was formulated into Paint B (described above). For each paint prepared with varying enzyme types and concentrations, the enzyme activity was determined by post-adding approximately 630 ppm of ethyl acrylate and monitoring its disappearance due to enzyme hydrolysis. The change in the EA content in the paint was determined by the procedure outlined above (Examples 1 and 2). The results are shown in Table 7, below, for two enzymes (Novozym™ CALBL and Novozym™ 51032) at enzyme concentrations of 0.01%, 0.1%, and 1.0% (% wet on wet addition to the latex).

TABLE 7

EA Content of the Paint at Time Intervals After EA Addition to the Paint.

| Enzyme Type | Amount of Enzyme | | | EA Content (ppm) at Time Interval After EA Addition | | | | Change (*) | % Change (*) |
|---|---|---|---|---|---|---|---|---|---|
| | % Added (Latex) | Latex (ppm) | Paint (ppm) | 0 Days | 1 Days | 6 Days | 9 Days | | |
| None | 0 | 0 | 0 | 612 | 624 | 597 | 585 | 27 | 4% |
| CALBL | 0.01 | 6 | 2.24 | 631 | 636 | 589 | 593 | 38 | 6% |
| | 0.1 | 60 | 22.4 | 654 | 635 | 526 | 479 | 175 | 27% |
| | 1.0 | 600 | 224 | 611 | 444 | 106 | 52 | 559 | 91% |
| N-51032 | 0.01 | 5 | 1.87 | 668 | 668 | 611 | 627 | 41 | 6% |
| | 0.1 | 50 | 18.7 | 656 | 535 | 167 | 87 | 569 | 87% |
| | 1.0 | 500 | 187 | 522 | 38 | 0 | 0 | 522 | 100% |

(*) Change and % change are 9 days after addition of EA into the enzyme treated paint.

The data show that for both of these enzymes, there is no significant residual enzyme activity when the enzyme is added at 0.01% (wet on wet) levels (equivalent to 5-6 ppm of solid enzyme on wet latex, or approximately 2 ppm of solid enzyme in the wet paint). However, for both enzymes there is significant residual activity for enzyme additions of 0.1% (wet on wet) levels (equivalent to 50-60 ppm of solid enzyme on wet latex, or approximately 20 ppm of solid enzyme in the wet paint).

Further data was obtained (in a different paint formulation, Paint C, Table 8, below) for both enzymes, and also for pig liver esterase, at the 0.05% (wet on wet) level (equivalent to 25-30 ppm of solid enzyme on wet latex, or approximately 10 ppm of solid enzyme in the wet paint), shown below (Table 9).

TABLE 8

Near-Zero VOC Paint Formulations for Paints C and D.

| Formulation Ingredient | Ingredient Type | Paint C Amounts (g) | Paint D Amounts (g) |
|---|---|---|---|
| Grind | | | |
| Water | Water | 37.4 | 37.4 |
| Tamol 731A (25% active) | Dispersant | 6.3 | 6.3 |
| BYK-024 | Defoamer | 0.80 | 0.80 |
| Tioxide R-TC90 | TiO2 Pigment | 105.6 | 105.6 |
| Satintone 5HB | Extender | 14.1 | 14.1 |
| Durcal 2 | Extender | 37.2 | 37.2 |
| LetDown | | | |
| Polymer B (48.7% solids)[1] | Binder | 189.5 | — |
| Rhoplex AC-261 (50.0% solids) | Binder | — | 192.4 |
| Texanol | Coalescent | — | 6.4 |
| Ropaque Ultra E (30% active) | Opaque Polymer | 34.3 | 34.3 |
| Acrysol RM-5 (30% active) | Thickener | 12.00 | — |
| Natrosol 250MHR (2.5% active) | | — | 2.6 |
| Water | Water | 104.8 | 104.8 |
| Totals: | | 542.0 | 544.0 |

[1] Polymer B prepared by the method of Example 3, except with composition: 38EHA/15BA/44MMA (<2% phosphoethyl methacrylate, and ureido methacrylate).

TABLE 9

EA Content of Paint C at Time Intervals After EA Addition to the Paint.

| Enzyme Type | Amount of Enzyme | | | EA Content (ppm) at Time Interval After EA Addition | | | Change (*) | % Change (*) |
|---|---|---|---|---|---|---|---|---|
| | % Added (Latex) | Latex (ppm) | Paint (ppm) | 0 Days | 1 Days | 4 Days | | |
| None | 0 | 0 | 0 | 436 | 421 | 431 | 5 | 1% |
| CALBL | 0.05 | 30 | 11.2 | 422 | 319 | 178 | 244 | 58% |
| N-51032 | 0.05 | 25 | 9.4 | 424 | 276 | 122 | 302 | 71% |
| PLE | 0.05 | 8 | 3.0 | 416 | 81 | 14 | 402 | 97% |

For all three enzymes, there is significant residual activity for enzyme additions of 0.05% (wet on wet) levels (equivalent to approximately 10 ppm of solid enzyme in the wet paint). The data show that the enzyme is still active in this paint formulation when added at levels of 0.05% (~10 ppm in the paint), and it is expected that degradation of paint properties is likely at these levels. Indeed, this level of addition of PLE or N51032 into an analogous paint formulation incorporating an HEC thickener (Natrosol™ 250 MHR Natrosol™ Plus 330) in place of the HEUR thickener (Acrysol™ RM-5) results in the paint setting up to a thick paste in less than 1 day. Similarly, at these levels, CALBL treated paint comprising HEC thickeners suffers unacceptable viscosity drift.

Example 7

Effect of Enzyme Level on Paint Formulation Stability

The use of enzymes to control odor in aqueous latex emulsion paints targets the level of organic carboxylester compounds present in the paint. This approach has no value to paint manufacturers if the critical properties of the paint are compromised. A stable rheology profile is one such critical property. Table 10, below, illustrates the effect on alcohol and ester VOC levels (and therefore odor of the paint), as well as KU viscosity, for a number of different enzymes added at various levels.

TABLE 10

Effect of Enzyme Level on Paint Formulation[1] Stability[2]

| ID[3] | Enzyme Type | Enzyme Level Latex (wet %) | Enzyme Level Latex (ppm) | Enzyme Level Paint (ppm) | Delta KU (1 week) RT | Delta KU (10 days) 50° C. | VOC Esters (ppm) | VOC Alcohol (ppm) | Ester Hydrolysis Activity (1 week) |
|---|---|---|---|---|---|---|---|---|---|
| 1-C | None | 0 | 0 | 0 | −2 | +4 | 15 | 94 | 0 |
| 2-C | CALBL | 1.0 | 600 | 212 | −7 | −18 | 0.2 | 104 | 0.0832 |
| 3-I | CALBL | 0.01 | 6 | 2.1 | −2 | −5 | 2.6 | 95 | 0.0116 |
| 4-I | CALBL | 0.005 | 3 | 1.1 | −2 | −5 | 4.5 | 96 | 0.0007 |
| 5-C | N51032 | 1.0 | 500 | 180 | +36 | Solid | 1.5 | 152 | 0.0746 |
| 6-C | N51032 | 0.05 | 25 | 8.8 | >+40 | Solid | 1.8 | 111 | 0.0532 |
| 7-I | N51032 | 0.005 | 2.5 | 0.9 | −2 | +6 | 1.7 | 116 | 0.0165 |
| 8-C | Lipex | 1.4 | 1000 | 350 | −1 | −6 | 0.3 | 117 | 0.0760 |
| 9-I | Lipex | 0.021 | 15 | 5.3 | −1 | −4 | 6.2 | 101 | 0.0121 |
| 10-C | Candida | 2.0 | 1000 | 350 | −1 | −4 | 14.5 | 95 | 0.0010 |
| 11-C | Candida | 0.5 | 250 | 88 | −1 | −2 | 14.2 | 97 | 0.0009 |

[1]Paint D (see Table 8).
[2]Block resistance was determined as described above, and was found to be acceptable (rating of 6 or higher in all categories) for all samples, except Paint 8, which had ratings of 1 for the 1 day hot block, indicating poor block resistance, 50-75% sealed).
[3]C = Comparative Example; I = Inventive Example.

Residual headspace ester levels as low as 10 ppm result in a detectable odor in waterborne paints, so acceptable low odor paints must have an ester VOC level less than 10 ppm, preferably less than 8 ppm, and even more preferably less than 5 ppm. The data show that addition of Candida fails to achieve acceptable odor levels for these addition levels of enzyme (for either 88 ppm or 350 ppm of enzyme in the paint). Moreover, the higher levels of Lipex 100L (for example, 350 ppm or higher in the paint) results in complete loss of block resistance.

Additionally, paint manufacturers require a stable paint with a KU viscosity change (delta KU) of no more than 8 KU, more preferably no more than 5 KU at room temperature, or 10 KU under heat aging conditions (simulated as 10 days at 50° C.). The data sets show that stable low odor paints are obtainable using CALBL or N51032 enzymes at levels of approximately 0.01% and lower (wet enzyme solution on wet latex; equivalent to approximately 2-6 ppm of solid enzyme in the latex, or approximately 1-2 ppm of solid enzyme in the paint). At these levels, the ester hydrolysis activity of the carboxylesterase enzyme is less than 0.03 micromole/minute.

Example 8

Enzyme Treatment of Ambient Cure Polymer Latex Comprising Hydrazide

As described earlier, ambient cure of paint films comprising a polymeric binder may be achieved wherein the emulsion polymer comprises polymerized units of a carbonyl containing monomer, and, optionally, the composition may further comprise a polyamine or polyhydrazide. Emulsion polymers of this type and methods to make such polymers, have been reported previously (see, for example, U.S. Pat. No. 4,250,070). An acrylic emulsion polymer composition obtainable by this method, comprised an acrylic polymer (45% solids), of composition: BA/MMA with Tg ~10° C. and less than 2% diacetone acrylamide, the composition further comprising less than 2% adipic dihydrazide (ADH).

Novozym™ CALB L (0.35 g of a 6% solution) was added to the acrylic emulsion polymer latex (3528 g). The mixture was shaken and allowed to stand at room temperature for 24 h. The residual ester content was reduced to zero (the level of the primary ester components in the latex, butyl acrylate and butyl propionate, were reduced from 16 ppm to 0 ppm, and 69 ppm to 0 ppm, respectively, as measured by GC).

The modified emulsion was formulated into a 21% PVC gloss paint and tested for gloss, block, stain resistance, alkyd adhesion and dirt pick-up. No significant deterioration of performance was observed. Residual hydrazine was also measured and found to be below detection limits, indicating that the enzyme does not hydrolyze the amide bond in the polyhydrazide.

Example 9

Combined Enzyme Treatment and Steam Stripping for VOC Removal

Enzyme treatment of an aqueous coating composition comprising an emulsion-polymerized addition polymer is more effective in removing carboxylester VOCs than conventional continuous process steam stripping. For example, it was found that 88% of carboxylester bulk VOCs were removed using just 6 ppm (solid enzyme on wet latex) of CALBL compared to a 50%, 70%, and 80% reduction after 1, 2, and 3 passes, respectively, of steam stripping. However, the combination of pre-treating the aqueous composition with enzyme (6 ppm of CALBL, contact for 16 days at room temperature) followed by steam stripping is particularly effective, reducing bulk VOCs by 95%, 96%, and 97%, after 1, 2, and 3 passes, respectively, of steam stripping.

Steam stripping actually becomes more effective in combination with enzyme treatment. For conventional steam stripping, VOCs that are more hydrophobic and normally retained in the polymer phase are more difficult to strip than VOCs that are more hydrophilic and contained in the aqueous phase. Carboxylesterase converts hydrophobic VOCs into constituent hydrophilic alcohols and acids. More facile removal by steam stripping lowers the overall VOC count for lower boiling components and creates a combination of VOCs that strips more easily. Moreover, the carboxylesterase, in converting the hydrophobic VOCs to hydrophilic VOCs, converts more odorous VOCs to less odorous compounds. As a result, it is easier to strip the composition to a lower odor with the same amount of steam because the material starts with a lower odor.

What is claimed is:

1. A low odor aqueous coating composition comprising:
    i) one or more emulsion-polymerized addition polymer;
    ii) one or more carboxylesterase enzyme having an ester hydrolysis activity in the composition of less than 0.03 micromole/minute;
    iii) one or more mono-alcohol with a formula molecular weight of less than 76; and
    iv) optionally, one or more organic carboxylester with a normal boiling point of less than 150° C.;
wherein the aqueous coating composition has a headspace volatile organic compound (VOC) content, as measured by headspace gas chromatography-mass spectrometry (GC-MS) at 33° C., of less than 10 ppm of the one or more organic carboxylester and more than 50 ppm of the one or more mono-alcohol.

2. The aqueous coating composition of claim 1, wherein the ester hydrolysis activity is less than 0.02 micromole/minute.

3. The aqueous coating composition of claim 1 having a headspace VOC content of less than 5 ppm of the one or more organic carboxylester.

4. The aqueous coating composition of claim 1 having a bulk VOC, by weight based on the total weight of the aqueous coating composition, of less than 1,000 ppm.

5. The aqueous coating composition of claim 1, wherein the one or more emulsion-polymerized addition polymer comprises an acrylic, styrene-acrylic, vinyl acetate-acrylic or vinyl acetate-ethylene emulsion polymer in an amount of at least 5% by weight of the emulsion polymer solids on total coating composition solids.

6. The aqueous coating composition of claim 1, wherein the one or more emulsion-polymerized addition polymer comprises polymerized units of a carbonyl containing monoethylenically unsaturated monomer.

7. The aqueous coating composition of claim 6, wherein the composition further comprises a polyamine or polyhydrazide.

* * * * *